(12) United States Patent
Ajaelo (10) Patent No.: US 11,076,986 B2
(45) Date of Patent: Aug. 3, 2021

(54) ELECTRONIC DROP DISPENSING DEVICE AND METHOD OF OPERATION THEREOF

(71) Applicant: Ikem C Ajaelo, Minnesota, MN (US)

(72) Inventor: Ikem C Ajaelo, Minnesota, MN (US)

( * ) Notice: Subject to any disclaimer, the term of this patent is extended or adjusted under 35 U.S.C. 154(b) by 607 days.

(21) Appl. No.: 15/811,670

(22) PCT Filed: May 12, 2016

(86) PCT No.: PCT/US2016/032229
§ 371 (c)(1),
(2) Date: Nov. 13, 2017

(87) PCT Pub. No.: WO2016/183394
PCT Pub. Date: Nov. 17, 2016

(65) Prior Publication Data
US 2018/0193190 A1 Jul. 12, 2018

Related U.S. Application Data (60) Provisional application No. 62/185,649, filed on Jun. 28, 2015, provisional application No. 62/159,995, filed on May 12, 2015.

(51) Int. Cl.
*A61F 9/00* (2006.01)
*A61M 5/168* (2006.01)
*G16H 20/13* (2018.01)

(52) U.S. Cl.
CPC .......... *A61F 9/0026* (2013.01); *A61F 9/0008* (2013.01); *A61M 5/1689* (2013.01); *G16H 20/13* (2018.01); *A61M 2205/8206* (2013.01); *A61M 2210/0612* (2013.01)

(58) Field of Classification Search
CPC .. A61M 2210/0612; A61M 2205/8206; A61M 5/1689; G16H 20/13; A61F 9/0008; A61F 9/0026
See application file for complete search history.

(56) References Cited

U.S. PATENT DOCUMENTS

| | | | |
|---|---|---|---|
| 7,883,031 B2 * | 2/2011 | Collins, Jr. | .......... A61M 11/005 128/200.14 |
| 8,474,083 B2 | 7/2013 | Reiter et al. | |
| 8,579,856 B2 * | 11/2013 | Sullivan | ................ A61M 15/08 604/118 |

(Continued)

*Primary Examiner* — Ariana Zimbouski
(74) *Attorney, Agent, or Firm* — White-Welker & Welker, LLC; Matthew T. Welker, Esq.

(57) ABSTRACT

Disclosed is a portable automatic electronic drop administration device and method of operation thereof. The device comprises a microcontroller communicatively coupled to at least an accelerometer and an electromechanical assembly to administer one or more drops of a liquid, semi-liquid or gaseous substance from any flexible container held within. The device detects whether it is in a suitable orientation before automatically self actuating the electromechanical assembly to administer one or more drops. It can be used in a variety of settings including self administration of eye drops, dispensing condiments or precise metering of liquid medications. Additionally, the device may contain sensors and wireless components to track usage and event data that may be communicated to a physician or other healthcare provider remotely.

17 Claims, 8 Drawing Sheets

(56) References Cited

U.S. PATENT DOCUMENTS

| | | | |
|---|---|---|---|
| 8,684,980 B2 * | 4/2014 | Hunter | A61B 5/0059 604/298 |
| 8,936,021 B2 * | 1/2015 | Collins, Jr. | A61M 11/005 128/200.14 |
| 9,170,148 B2 | 10/2015 | Bayley et al. | |
| 9,311,806 B2 | 4/2016 | Hazen et al. | |
| 9,463,412 B2 | 10/2016 | Akdogan et al. | |
| 9,476,902 B2 | 10/2016 | Temko et al. | |
| 9,483,930 B1 | 11/2016 | Haaland | |
| 9,504,360 B2 | 11/2016 | Diepen | |
| 9,504,826 B2 | 11/2016 | Flyash et al. | |
| 9,506,798 B2 | 11/2016 | Saltzgiver et al. | |
| 9,507,916 B2 * | 11/2016 | Charania | G06F 19/3462 |
| 2002/0049389 A1 * | 4/2002 | Abreu | A61B 5/14546 600/558 |
| 2007/0211212 A1 * | 9/2007 | Bennwik | A61B 3/0008 351/221 |
| 2012/0330228 A1 * | 12/2012 | Day | A61M 5/14248 604/82 |
| 2013/0038690 A1 * | 2/2013 | Mitchell | H04N 13/211 348/46 |
| 2013/0078625 A1 | 3/2013 | Holmes et al. | |
| 2013/0085459 A1 * | 4/2013 | Voss | A61B 3/10 604/290 |
| 2013/0085460 A1 * | 4/2013 | Voss | A61M 11/005 604/290 |
| 2014/0213989 A1 * | 7/2014 | Kelly | A61F 9/0026 604/296 |
| 2014/0228783 A1 * | 8/2014 | Kraft | A61F 9/0008 604/300 |
| 2014/0350490 A1 * | 11/2014 | Korodi | A61F 9/0026 604/290 |
| 2015/0005721 A9 | 1/2015 | Voss et al. | |
| 2015/0018781 A1 * | 1/2015 | Rinderknect | A61M 11/005 604/298 |
| 2015/0057623 A1 | 2/2015 | Hyde et al. | |
| 2015/0112286 A1 * | 4/2015 | Claret | A61F 9/0008 604/296 |
| 2015/0359667 A1 * | 12/2015 | Brue | H04L 67/12 604/295 |
| 2016/0279652 A1 | 9/2016 | States et al. | |

\* cited by examiner

|  | SENSOR 1 (SCLERA) | SENSOR 2 (IRIS) |
| --- | --- | --- |
| EYELID OPEN | R -227, G - 235, B - 248 | R -148, G - 82, B - 0 |
| EYELID CLOSED | R -229, G - 212, B - 153 | R -229, G - 208, B - 136 |

Fig. 7

| AXIS | LEFT EYE | RIGHT EYE |
| --- | --- | --- |
| X | -0.1406g | 0.1432g |
| Y | -0.5508g | -0.5522g |
| Z | 0.7930g | 0.7935g |

Fig. 8

Eye Medication Journal

Tuesday, May 8, 2015. 00.30am
Timolol 1 drop left eye
Time to administration: 3 minutes
Number of attempts: 4
Blink event: three
Dosage remaining: 10 days

Tuesday, May 8, 2015. 00.35am
Timolol 1 drop right eye
Time to administration: 1 minute
Number of attempts: 1
Blink event: None
Dosage remaining 9.5 days

Fig. 9

ELECTRONIC DROP DISPENSING DEVICE AND METHOD OF OPERATION THEREOF

CLAIM OF PRIORITY

This application claims the benefit of priority under 35 U.S.C. § 365 of International Patent Application Serial No. PCT/US2016/032229 filed on May 12, 2016, designating the United States America, which in turns claims the benefit of priority to U.S. Provisional Patent Application Ser. No. 62/159,995, filed 12 May 2015 and U.S. Provisional Patent Application Ser. No. 62/185,649 filed 28 Jun. 2015, the entire disclosures of which are hereby expressly incorporated by reference herein.

TECHNICAL FIELD

This disclosure relates generally to data processing devices and, more particularly, to an electronic drop-dispensing device and method of operation thereof.

BACKGROUND ART

Today most liquid medicines, foods, oils, milk, condiments, lotions, creams, sanitizers, cleaning solutions, perfumes, soaps, shampoos, toothpastes come in plastic containers and increasingly flexible pouches/bags. Dispensing the contents of these enclosures is a manual process sometimes requiring two hands and a high degree of dexterity to ensure the enclosed material is expelled correctly. This can be difficult depending on the density of the enclosed material and the wall thickness of the enclosing bag or container.

This has spurred a category of mechanical assistive devices to help people who may have difficulties using traditional plastic bottles and containers as part of their daily activities. Some of these devices are used as an aid to help dispensing condiments like ketchup, while others are used to help with pouring food ingredients like pancake batter while cooking. Some are used in the bathroom for pouring soaps or dispensing creams and lotions.

However the mechanical assistive devices that currently exist are manual, thus requiring the user to initiate (trigger) the release of fluids or drops of fluid. They typically do not have any controls built in to maintain precision and accuracy while in use.

Eye drop medications are a vexing example of this. Since eye drops were developed over a century ago, it has been well known that many people have difficulties instilling the right amount of medication into their eye(s). This is particularly true for elderly individuals who have reduced baseline vision and also suffer from chronic diseases such as arthritis that impact their ability to manipulate standard eye drop containers.

A wide variety of techniques and devices have been developed and marketed to address these challenges, but many are fraught with problems ranging from unwieldy design, complex and confusing instructions, amongst many other shortcomings. The biggest drawback for all of the available devices is that they still require the user to manually control the release of the precise amount (usually one eye drop) while simultaneously trying to direct the eye drop bottle into the exact position over the eye. The result is that even today up to two-thirds of individuals fail to properly use their eye drop medications as instructed, resulting in a worsening of the disease state in the affected eye(s), ultimately resulting in blindness.

In addition to the challenges of using eye drops at home, treating eye injuries is also difficult because there is not a safe and reliable method of delivering eye drop anesthetic medications to the eye in an outpatient setting. Injuries to the eye(s) of any type are extremely painful and often require constant pain relief for the first few days. Many anesthetic agents are available to achieve proper corneal anesthesia, such as proparacaine, cocaine, procaine, tetracaine, hexylcaine, bupivacaine, lidocaine, benoxinate, mepivacaine, prilocaine and etidocaine. These anesthetics work by blocking nerve function in the cornea and conjunctiva. Many of these medications provide full relief in as little as fifteen seconds and can last fifteen to twenty minutes. However, it is well known that these anesthetic medications can cause delayed healing with repeated use. Other common complications include corneal ulcers, corneal swelling, corneal perforations amongst others.

For this reason, and because we cannot automatically control the usage of these medications in an outpatient setting, it is currently standard medical practice to not prescribe these medications for home use despite their well-proven therapeutic effects. Alternately, other classes of topical ophthalmic agents (cycloplegics, mydriatrics, non-steroidals) and/or oral pain killers (Tylenol®, hydrocodone, oxycodone, etc.) are utilized. However, the therapeutic relief provided is suboptimal in comparison to the topical ophthalmic anesthetic agents listed previously.

But these challenges are not just limited to the eye. As mentioned earlier, most liquid products and medicines are delivered in some type of plastic/flexible pouch enclosure. Some of the contents of these enclosures must be delivered in precise amounts. Additionally, some of these products are extremely toxic and lethal if taken in any amount that exceeds their prescribed dosing schedule. So they must be used by and only accessible by a responsible adult.

Children's oral liquid medications are a great example of this. Due to the palatability of the contents, it is a well known fact that children as young as a few months will play with liquid bottle medications. They have been known to ingest some or all of the contents of these bottles. Every year, around the world, there are thousands of emergency room visits and hospitalizations due to accidental ingestions of prescription and over the counter liquid medications. Some of these children will unfortunately die or suffer long term morbidity. A number of initiatives have been developed over the years to prevent these ingestions. These include stiffer bottle walls, child proof bottle caps and inclusion of dispensing nozzle tips that require a syringe to withdraw the medication contents. While impactful, it still has not stopped the thousands of overdoses that occur each year. In addition, and quite paradoxically, as these plastic bottles become safer, the more unwieldy they become particularly noticeable if you have arthritis or have lost dexterity of your hands for any reason.

Thus, given the high morbidity and mortality associated with accidental overdoses of these medications, and the significant challenges with using these bottles, there exists a need for a safe, automatic, easy-to-use and accurate means of dispensing oral liquid medications. The device must ensure it is only accessible by the individual who needs it. It must deliver the precise amount of contents when required and should be controllable not only at the point of usage but also remotely.

In virtually any environment that demands a precise amount of contents from a handheld device or bottle, a portable automatic accurate delivery device is required. This could be an individual who has lost use of their upper limbs but still needs a certain amount of ketchup at dinner time. It could also be a parent who needs a precise amount of liquid medication for a child. It could be an astronaut in space who needs a precise amount of liquid dispensed at any particular time. These scenarios and many more require a portable automated electronic liquid or drop delivery device.

SUMMARY

Disclosed are an electronic drop dispensing device and method of operation thereof. Such a device may be used for liquids such as eye drop medications, oral liquid medications, saline, water, liquid supplements, soaps, shampoos, sanitizers, cleaning solutions, or even semi-liquids such as gels, lotions, condiments, creams, toothpastes or even gaseous and vaporized contents.

In one aspect, an apparatus for electronically administering drops comprises a microcontroller communicatively coupled to an accelerometer. The apparatus also comprises a housing suitable for accommodating the microcontroller, and optionally, a drop-dispenser container. The apparatus additionally comprises an electromechanical compressing assembly disposed within the housing communicatively coupled to the microcontroller such that operation of the electromechanical compressing assembly causes the electromechanical compressing assembly to gradually push against the external wall of the drop-dispenser container. Upon detection of a predetermined orientation of the apparatus through the accelerometer, the microcontroller is configured to automatically operate the electromechanical compressing assembly to compress the drop-dispenser container to a calculated degree such that said compression of the drop-dispenser container causes the drop-dispenser container to administer one or more drops of liquid or non-liquid substances contained within the drop-dispenser container.

The apparatus may further comprise one or more color sensors communicatively coupled to the microcontroller. The one or more color sensors may be configured to detect a color of a portion of the drop-dispenser container. Said color may be associated with the identification of the substance contained within the drop-dispenser container or the capacity level of the drop-dispenser container. Operation of the microcontroller may additionally depend on an approximate match between the color and a predetermined range of colors.

The apparatus may also comprise a wireless interface communicatively coupled to the microcontroller. The wireless interface may be configured to communicate event data generated by the microcontroller to a network-enabled data processing device directly or over a network. The event data may comprise any information including: a type of medication contained within the drop-dispenser container, dosage information, occurrence of blink events, remaining dosage, number attempts to administer a dose, time of administration of dosage, and time to administer dosage, time to refill medication and time to re-order medication.

The apparatus may further comprise a display screen communicatively coupled to the microcontroller for displaying patient-related information. Such patient-related information may comprise physician-recommended dosage, drop administration reminders, or other information pertaining to proper patient care.

If the device is configured to dispense eye drops either as an eye drop assist device or as a drug-device combination, the housing may comprise a curved rim configured to adapt to the rim of the bony eye socket. Beneath the curved rim may consist of a curved floor comprising one or more passageways to transmit light from the eyes to color sensors. The one or more passageways may be optionally fitted with a lens for focusing light to the one or more color sensors.

In another aspect, a method of administering drops through an electronic drop-dispensing device comprises detecting, through a microcontroller communicatively coupled to an accelerometer, a predetermined orientation of the electronic drop-dispensing device. Based upon detecting the predetermined orientation, the method also comprises operating, through the microcontroller, an electromechanical compressing assembly communicatively coupled to the microcontroller such that operation of the electromechanical compressing assembly causes the electromechanical compressing assembly to compress the drop-dispenser container such that said compression causes the drop-dispenser container to administer one or more drops of liquid or non-liquid substances contained within the drop-dispenser container. Operating the electromechanical compressing assembly may be additionally based upon detecting an approximate match between a color detected by one or more color sensors communicatively coupled to the microcontroller and a predetermined range of colors.

The method may also comprise displaying, through a display screen communicatively coupled to the microcontroller, patient-related information, such as physician-recommended dosage, drop administration reminders, or other information pertaining to proper patient care. The method may further comprise generating event data through the microcontroller. Such event data may comprise one or more of the following: a type of medication contained within the drop-dispenser container, dosage information, occurrence of blink events, remaining dosage, number of attempts to administer a dose, time of administration of dosage, time to administer dosage and time to refill medication and time to re-order medication. The method may also comprise communicating, through a wireless interface communicatively coupled to the microcontroller, the event data to a network-enabled data processing device directly or over a network.

In another aspect, a method of distinguishing drop administration to a right eye and a left eye comprises detecting an orientation of a drop-dispenser container during drop administration through one or more sensors communicatively coupled to a microcontroller. The method further comprises determining whether the drop-dispenser container was held against a right eye or a left eye based on a comparison of the orientation indicia of the drop-dispenser container to predetermined orientation indicia for the right eye and the left eye.

In another aspect, a method of detecting blink events during or after a drop administration comprises detecting one or more colors of an eye through one or more color sensors communicatively coupled to a microcontroller. The method further comprises determining whether a blink event occurred based on an approximate match between the one or more colors and a predetermined range of colors.

In a further aspect, a drug-device combination apparatus for electrically administering one or more drops comprises a microcontroller communicatively coupled to an accelerometer. The drug-device combination also comprises a housing suitable for accommodating the microcontroller, the accelerometer, and any medication container. The drug-device combination also comprises an electromechanical compressing assembly disposed within the housing communicatively coupled to the microcontroller such that operation of the electromechanical compressing assembly causes the electromechanical compressing assembly to gradually push against the external wall of the medication container. Upon detection of a predetermined orientation of the apparatus through the accelerometer, the microcontroller is configured to operate the electromechanical compressing assembly to compress the medication container to a calculated degree. Such compression of the any medication container, cartridge, bag or reservoir self-actuates the release and administration one or more drops of liquid or non-liquid substances contained within the drug-device.

The drug-device combination apparatus may also comprise one or more color sensors communicatively coupled to the microcontroller. Operation of the microcontroller may additionally depend on an approximate match between the color and a predetermined range of colors. The drug-device combination apparatus may also comprise a wireless interface communicatively coupled to the microcontroller. The wireless interface may be configured to communicate event data generated by the microcontroller to a network-enabled data processing device directly or over a network. The event data may comprise any of the following: a type of medication contained within the drop-dispenser container, dosage information, occurrence of blink events, remaining dosage, number of attempts to administer a dose, time of administration of dosage, and time to administer dosage. The drug-device combination apparatus may also comprise a display screen communicatively coupled to the microcontroller for displaying patient-related information, such as physician-recommended dosage, drop administration reminders, or other information pertaining to proper patient care.

If the drug-device combination device is configured to dispense eye drops, the housing of the drug-device combination apparatus may also comprise a curved rim adapted to fit the bony eye socket of the eye. The drug-device may include a curved floor. The curved floor may comprise one or more passageways for improving consistency in detection of the color. The one or more passageways may be optionally fitted with a lens for focusing light to the one or more color sensors.

BRIEF DESCRIPTION OF THE DRAWINGS

The embodiments of this invention are illustrated by way of example and not limitation in the figures of the accompanying drawings, in which like references indicate similar elements and in which.

Other features of the present embodiments will be apparent from the accompanying drawings and from the detailed description that follows.

REFERENCE LIST FOR DRAWING LABELS

Electronic drop device 100
Color sensor 102
Color sensor 104
Color sensor 106
Electronic control unit 108
Servo 110
Lever arm 112
Accelerometer 114
Bluetooth module 116
Piezo buzzer 118
Battery 120
Display screen 122
LED indicator 124
Housing 126
Drop container 200
Curved rim 201
Curved floor 202A, B
Eye 204
Passageway 206A, B
Lens 208A, B
Eye drops 210
Central opening 212
PCB 214
Rear opening 216
Rigid floor 218
Servo shaft 220
Gear 222
Rack 224A, B
Nozzle 300

DETAILED DESCRIPTION

The detailed description set forth below in connection with the appended drawings is intended as a description of various configurations of the electronic drop device and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Definitions

"Drop device" refers to a device for administering drops of any liquid, semi-liquid, or gaseous substance using any mechanical or electromechanical means.

"Drops" refers to the smallest amount of fluid that can be dispensed from a standard compressible bottle of liquid under gravity typically 20-70 microliters. The drops may be dispensed individually or depending on the device may dispensed rapidly and/or under pressure to dispense a lump or continuous stream of material.

"Drug-device" refers to any device containing a drug of any type, shape or form wherein the drug cannot be separated from the device.

Nozzle refers to any hole or orifice on any medication container, bag, reservoir or cartridge through which the medication contents are finally dispensed to its target.

"Electronic control unit" refers to a microcontroller or a system on a chip (SoC) typically comprising at least a processing unit and at least a memory (volatile and/or non-volatile memory).

"Eye drop medication" refers to any class of ophthalmic medications including but not limited to anti-infectives, anti-inflammatories, steroids, nonsteroidal anti-inflammatories, cholinergic agonists, alpha-adrenergic agonists, beta-adrenergic receptor antagonists, carbonic anhydrase inhibitors, mydriatics, cyclopegics, miotics, corticosteroids, prostaglandins, prostaglandin analogues, immunosuppressives, calcium channel blockers, beta blockers, anti-inflammatory compounds, antimicrobial anesthetics, diagnostic agents, ocular lubricants (artificial tears), viscosifying agents. Examples of these medications include but are not limited to pilocarpine, acetylcholine, carbachol, timolol, dorzolamide, latanoprost, phenylephrine, tropicamide, atropine, cyclopentolate, ciprofloxacin, ofloxacin, trifluridine, proparacaine, tetracaine, various over-the-counter (OTC) eye medications, and more. The term also applies to any class or type of ear or nasal drop medications.

"Drop container" refers to any compressible vessel or reservoir of any material, shape and form designed to dispense of all of its contents. It may include but not limited to any type and combination of plastic, any type and form of flexible pouches or enclosure made with laminate lining, any type or form of paper, any type or form of cardboard or any type or form of compostable or biodegradable material. The material could be natural, organic, synthetic or semi-synthetic. The walls of the vessel may be in a standard curvilinear form with a standard neck or may be bellows shaped with or without a neck or a combination thereof.

"Blink event" refers to an event during which one or more eye(s) close and open or refers to a momentary closed state of one or more eye(s).

"Medical environments" include, but are not limited to, ocular examinations, ocular surgery, ocular pressure measurements, ocular treatments, ocular monitoring, sleep detection, sleep monitoring, driver alertness, fatigue detection, control and usage of any devices by handicapped or disabled individuals.

"Electronic compressing assembly" refers to any combination of electronic, mechanical, or electromechanical devices used to press against another object. The devices may work alone or may work as part of an assembly such as a rack and pinion system or ball screw assembly.

Elements described herein as coupled have an effectual relationship realizable by a direct connection or indirectly with one or more other intervening elements.

Disclosed herein is an electronic drop dispensing device and method of operation thereof for automatically administering, tracking and monitoring administration of drops from a drop container. It is contemplated for use in any number of medical or non-medical environments. It is also expected that the principles applied may also be applicable to any liquid, in any physical state (gel, gas, vapor, lotion, etc.) in any compressible vessel, for any function, including but not limited to ear drop administration, nasal drop administration, administration of liquid oral medications (Tylenol®, Motrin®, etc.), hand and skin application of any soaps, sanitizers, creams, lotions, perfumes, and to facilitate the release of foods and condiments from any compressible vessel (e.g. astronaut food). It may be used in different terrestrial environments above and below ground level including underwater, in a vacuum, in the air or in space. As a drug-device, it may be utilized in various circumstances such as to administer corneal anesthesia utilizing standard anesthetic ophthalmic medications in an outpatient or home setting. The detection of a blink event and all other principles described herein may be used for drug trials and medical research to verify compliance and adherence with any ophthalmic medication regimen.

In one embodiment as disclosed below, the electronic drop device may be configured as an ophthalmic drop device to dispense and track the administration of any topical ophthalmic anesthetic. Most if not all the principle features of an automatic electronic drop device dispenser will become apparent including including the precise and accurate detection of when an eye is open and when the head is in a proper position, precise and accurate expulsion of any amount of drops as required, recording and monitoring all events during any administration of the drop, identification of the type of contents dispensed as well as tracking refills to name a few.

Figure 1:
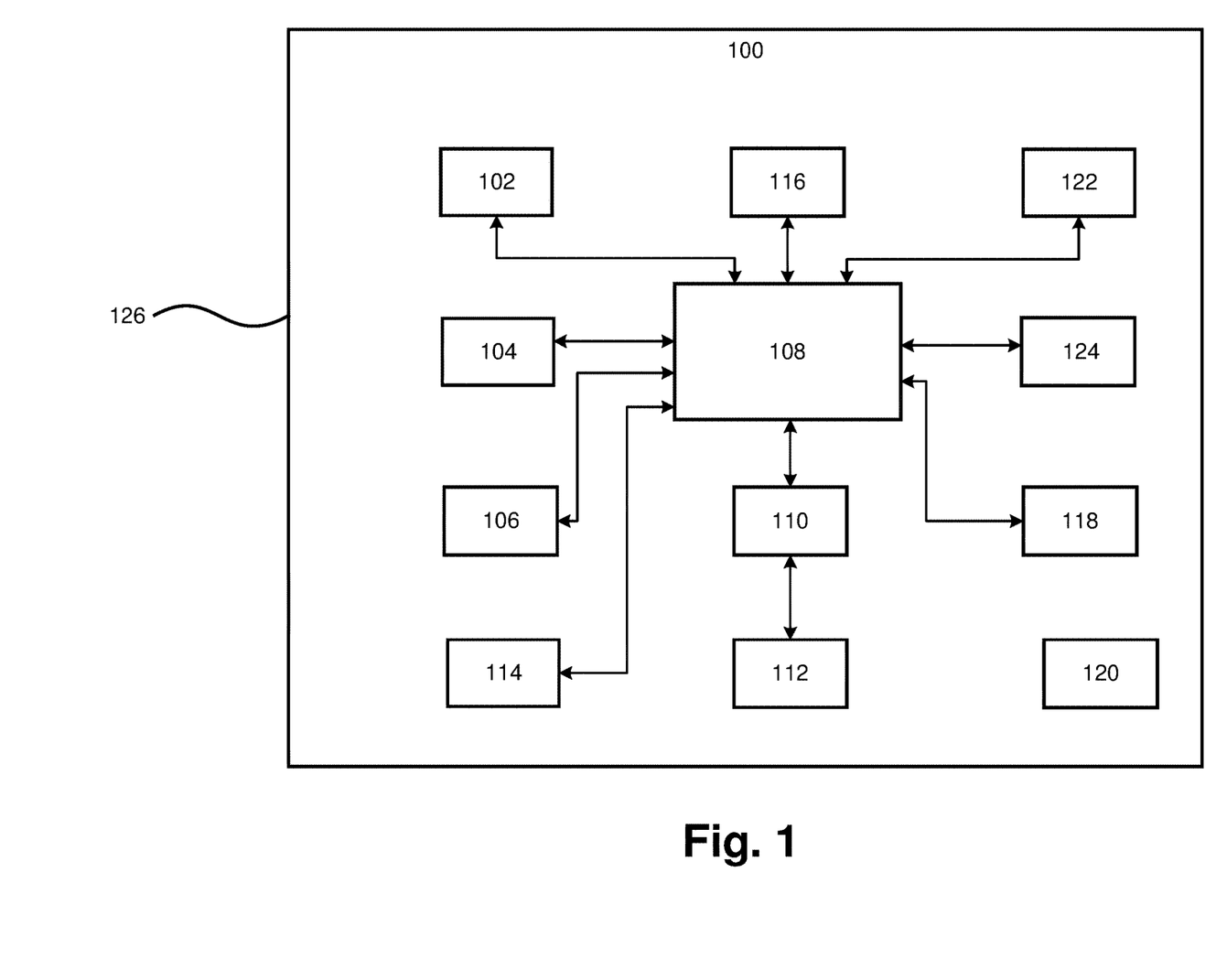
FIG. 1 is a block diagram of an electronic drop device showing internal components and interactions thereof, according to one or more embodiments.

Reference is now made to FIG. 1, which is a block diagram of an electronic drop device 100 showing internal components and interactions thereof, according to one or more embodiments. In one embodiment, the electronic drop device 100 may comprise color sensor 102, color sensor 104, and color sensor 106 communicatively coupled to an electronic unit 108. The electronic unit 108 may be subsequently communicatively coupled to a servo 110, an accelerometer 114, a Bluetooth® module 116, a piezo buzzer 118, a battery 120, a display screen 122, and a light-emitting diode (LED) indicator 124. The servo 110 may be subsequently coupled to a lever arm 112. Alternatively the servo 110 may be coupled to one or more racks 224 A, B in a rack and pinion type of assembly. For ease of description, the servo 110 and the lever arm 112 or rack 224 A, B may be referred to collectively as the electromechanical compressing assembly 110. The Bluetooth® module 116 may be referred to broadly as a wireless interface 116 and may also be a Wi-Fi™ chip or any other wireless interface including RFID and UWB.

The electronic drop device 100 may comprise a housing 126 that may be any size or shape and may be made of any material suitably rigid to prevent manipulation of the housing 126, any compressible region of the electronic drop device 100, or the internal components of the electronic drop device 100. Suitable materials for the housing 126 include but are not limited to plastic, any form of steel, any type of wood, any form of fiberglass, any form of metal or metal alloy or any combination thereof.

The color sensor 102, color sensor 104, and color sensor 106 may be any light-sensing device capable of detecting color, including but not limited to photocells, photomultipliers, photodiodes, phototransistors, ambient light sensors, photoconductive sensors, optical integrative circuits or any hybrid combination thereof. In a preferred embodiment, the color sensors 102-106 may each be the TCS3472 color light-to-digital converter provided by AMS-TAOS USA Inc. The color sensors 102-106 may return red (R), green (G), and blue (B) values (filtered) and/or clear (unfiltered) light sensing values and may also provide an infrared (IR) blocking filter. The color sensors 102-106 allow for precise measurement of any color under varying lighting conditions and through attenuating materials. The color sensors 102-106 may be integrated in a printed circuit board (PCB)(PCB 214 in FIG. 1) of the electronic drop device 100. Alternately, the color sensors 102-106 may be an all-in-one color sensor such as the flora color sensor from Adafruit (TCS34725). The color sensors may measure the color of any material placed in front of them with a high degree of sensitivity and discrimination using either ambient light (preferred) or direct illumination of the object.

The electronic control unit 108 may be any suitable microcontroller but preferably may comprise an Atmel ATmega328 single-chip microcontroller integrated in a PCB of the electronic drop device 100. The electronic control unit 108 may comprise an inter-integrated circuit (I2C) and may also support digital/analog I/O integration with the Bluetooth® module 116 and the accelerometer 114. The Bluetooth® module 116 may be any suitable Bluetooth® transceiver, such as the Texas Instruments® CC2540 Advanced Bluetooth® 4.0 module providing a low energy means of transmitting data to any Bluetooth®-capable device. Other types of Bluetooth® modules may be used, using regular Bluetooth® 4.0 (not low-energy) or any older Bluetooth® standard (such as Bluetooth® 3.0). The accelerometer 114 may be any suitable 3+-axis accelerometer with or without a tilt sensor, gyroscope, magnetometer, velocimeter, and/or built-in GPS tracker (or other satellite positioning system), such as the Bosch Sensortech® BMA250 which may subsequently communicated with the Bluetooth® module 116 and/or the electronic control unit 108. An example of a PCB incorporating the above preferred modules may be the LightBlue® Bean or LightBlue® Bean+. Powering the device may be any suitable battery 120, such as a lithium ion or lithium polymer 3-volt battery with at least 1500 mAh storage capacity.

Figure 2:
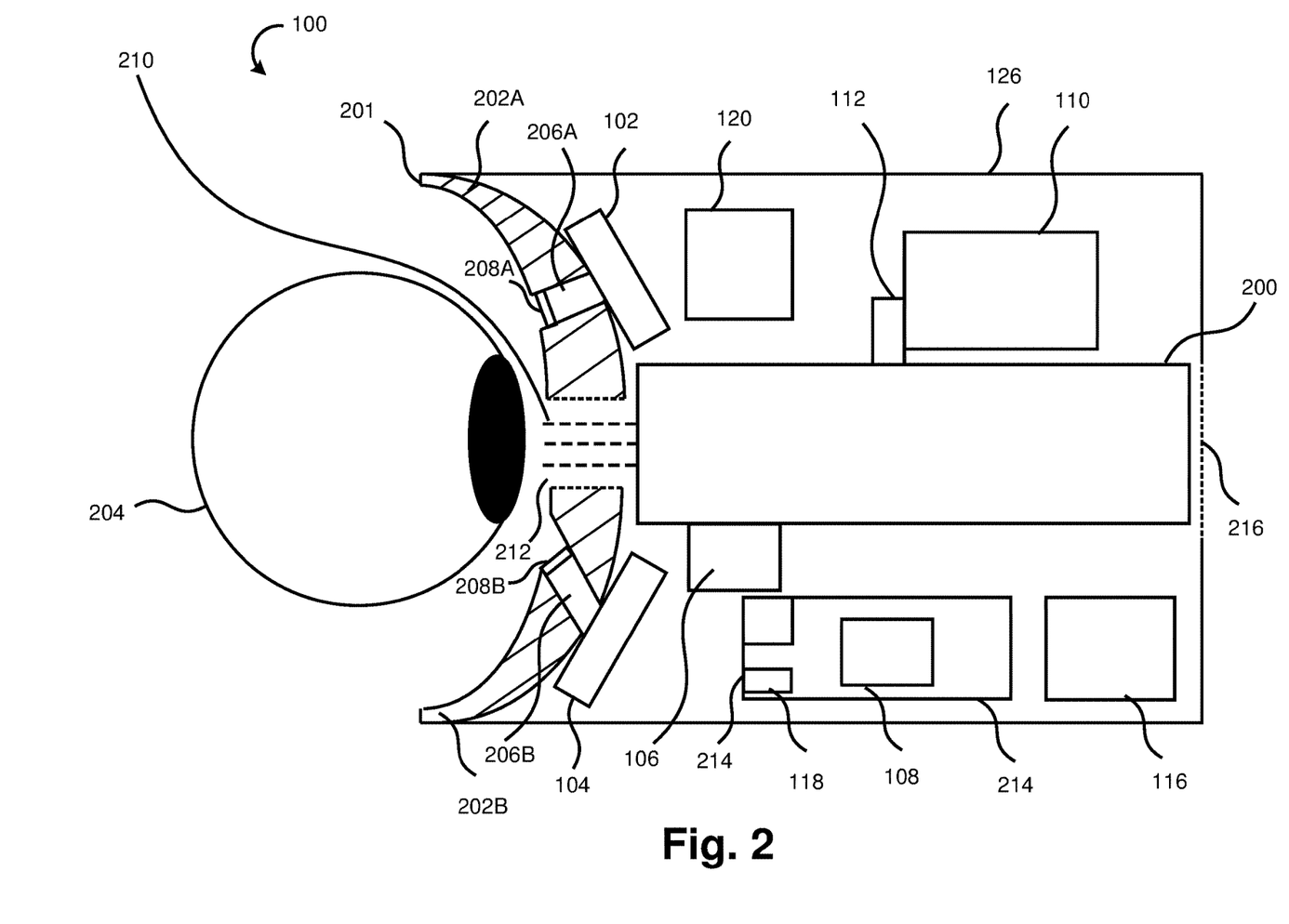
FIG. 2 is a schematic view of the electronic drop device of FIG. 1, according to one or more embodiments.

Reference is now made to FIG. 2, which is a schematic view of the electronic drop device 100 of FIG. 1, according to one or more embodiments. The housing 126 of the electronic drop device 100 may be structurally designed in a way suitable for accommodating a drop container 200 partially or fully within the housing 126. The drop container 200 may contain any type and form of eye drop medication or other liquid, semi-liquid, or gas. For example, the drop container 200 may be any traditional multi-dose eye drop bottle of any milliliter (mL) size, shape, and material or a single-dose, preservative-free vial of any size, shape, or material.

In one embodiment in which the drop container 200 is fully contained within the housing 126, the interior walls of the housing 126 may be coated with an adhesive or cement compound of any type of formulation that may chemically bind to the outer walls of the drop container 200 to create an irreversible and/or tamper-proof bond, thereby preventing any direct access to the drop container 200. An exemplary compound would be the Weld-on 3 acrylic plastic cement from IPS Corporation in Compton, Calif.

In another embodiment, the drop container 200 may be insertable through a rear opening 216 of the housing 126. When the drop container 200 is emptied through operation of the electronic drop device 100, the drop container 200 may be pulled out from the rear opening 216 and another drop container (not shown in the Figures) may be inserted through the rear opening 216 such that the nozzle 300 of the replacing drop container 200 is positioned at the central opening 212.

In yet another embodiment, when the front opening 212 and drop container 200 are equally sized, the drop container 200 may also be inserted through the front opening 212 of the housing 126 such that the nozzle 300 of the drop container is positioned at the central opening 212. The drop container 200 may be removed by pulling forward the nozzle 300 of the drop container 200.

The curved rim 201 may be structurally shaped to adapt and follow the bony rim of the eye socket to provide a fixed position for operation as well as accommodate positioning of an eye 204 substantially in the view of the color sensor 102 and the color sensor 104. Other structural shapes for accommodating positioning of other facial features or body parts may be used instead and are within the scope of the exemplary embodiments described herein. The color sensor 102 and the color sensor 104 may be positioned substantially to one side of the interior of the housing 126. In one embodiment, the color sensor 102 may be positioned near or coupled to a first portion of a curved floor 202A and the color sensor 104 may be positioned near or coupled to a second portion of the curved floor 202B.

Figure 4:
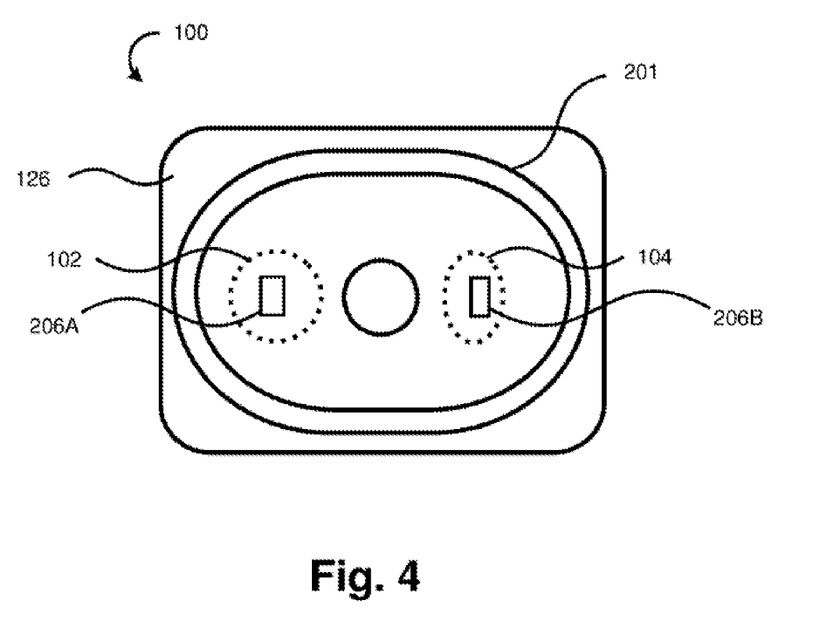
FIG. 4 is a top plan view of the electronic drop device of FIG. 1 showing the internal position of color sensors within the electronic drop device, according to one or more embodiments.

The upper portion of the curved floor 202A and the lower portion of the curved floor 202B may comprise a first passageway 206A and a second passageway 206B respectively. Reference is now made to FIG. 4, which is a top plan view of the electronic drop device 100 of FIG. 1 showing the internal position of color sensor 102 and color sensor 104 within the electronic drop device 100, according to one or more embodiments. The first passageway 206A may be angled so as to provide the color sensor 102 a view to the sclera of the eye 204. The second passageway 206B may be angled so as to provide the color sensor 104 a view to the iris of the eye 204. As such, the curved floor 202A, B allows the color sensor 102 and the color sensor 104 to detect the visible color rays reflected from only the sclera and the iris of the eye 204. To ensure accurate readings, the walls of the first passageway 206A and the second passageway 206B may be lined with a dark-colored material to minimize the impact of surrounding colors on the readings of the color sensor 102 and the color sensor 104. The accuracy may be further enhanced by the placement of magnifying lenses 208A-B within the passageways 206A-B and between the color sensors 102-104 and the eye 204, thereby increasing the amount of light reaching the color sensor 102-104 from each region of the eye 204.

Any number and type of servos (such as the continuous rotational or stepper servos from Adafruit) may be used for servo 110, which may be operably coupled to the lever arm 112 (or compressing arm) disposed such that the operation of the servo 110 causes the lever arm 112 to gradually compress the drop container 200 and force ejection of one or more eye drops 210 through a central opening 212 in the curved floor 202A, B.

Since current drop containers have varying wall thicknesses, and almost all require increasing amounts of force to eject the same drops 210 as the drop container 200, an advantage of the exemplary embodiments is the ability to increase the amount of force exerted on the walls of the drop container 200 with successive drops. By increasing the angle of movement of the lever arm 112, the amount of force exerted on the walls of the drop container 200 may be increased. This ensures that one drop 210 or as many as needed (or as prescribed by a physician) may be ejected each time.

In an alternative embodiment, the servo 110 may work without a lever 112 but exert the same force on the drop container 200 by pushing a rigid floor 218 attached to the servo 110 which compresses the drop container 200. Attached to the shaft 220 of the servo 110, could be one or more gears (pinion) 220 which rotate on one or more racks 224 A,B in a rack and pinion assembly causing movement of a rigid floor that gradually compresses the drop container 200. The drop container 200 could be a standard plastic bottle, a flexible pouch or reservoir or preferably a bellows collapsible type of bottle.

In either embodiment, the actual degrees of rotation of the servo 110 when activated is determined by the application and prior testing data. The amount of displacement of the drop container 200 required to dispense one drop under gravity is tested and stored by the electronic control unit 108. When one drop is required for instance, the servo 110, is configured on command by the electronic control unit 108 to rotate the absolute number of revolutions that will produce the same amount of displacement of the walls of drop container 200 required to dispense one drop from the drop container 200. If several drops or a stream of drops or fluid are required, the equivalent degrees of rotation are completed by the servo 110.

Figure 3A:
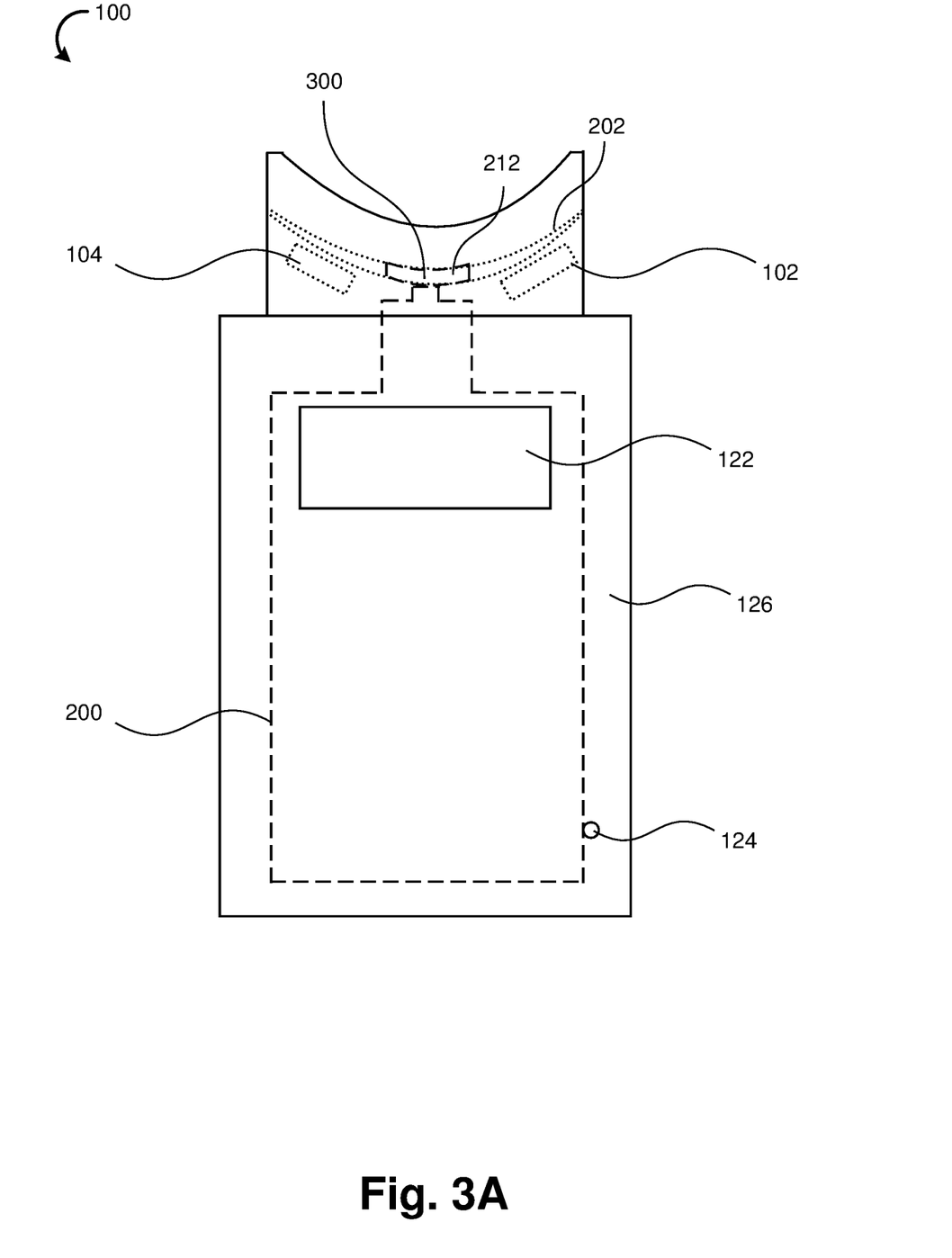
FIG. 3A is a front elevational view of the electronic drop device of FIG. 1, showing the internal positioning of a drop container and one or more color sensors within the electronic drop device, according to one or more embodiments.
Figure 3B:
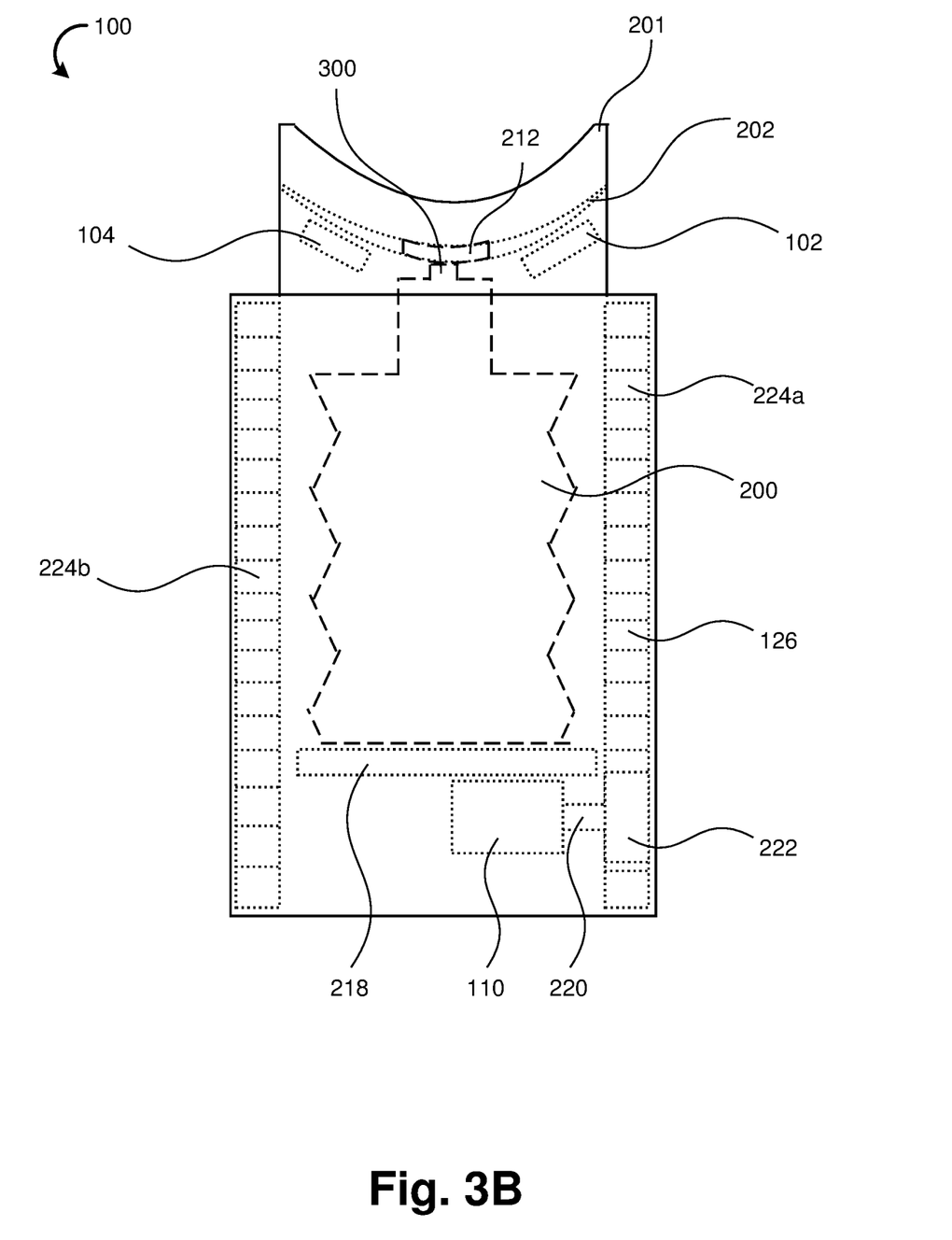
FIG. 3B is another front elevation view of the electronic drop device of FIG. 1 according to another embodiment, showing the internal positioning of a bellows type drop container flanked by two racks.

Reference is now made to FIG. 3A, which is a front elevational view of the electronic drop device 100 of FIG. 1, showing the internal positioning of a drop container and one or more color sensors 102, 104 within the electronic drop 100 device according to one or more embodiments. The display screen 122 may be embedded within or coupled on the surface of the housing 126. The display screen may be an liquid crystal display (LCD) or LED display. The electronic drop device 100 may also comprise an LED indicator 124 embedded within the housing 126. Whereas the display screen 122 may display messages (such as patient-related information, recommended dosage information, administration reminders, or instructions on how to use the electronic drop device 100), the LED indicator 124 may indicate reminders or other information through the use of a multi-color LED using an intermittently flashing pattern or other arrangement.

Reference is now made to FIG. 3B, which is another front elevation view of the electronic drop device 100 of FIG. 1 according to another embodiment, showing the internal positioning of a bellows type drop container 200 flanked by two racks 224 A,B which together along with the servo 110 and gear 222 provide a mechanical assembly for the upward movement of the servo to gradually compress the drop container 200. The display screen 122 and LED indicator 124 has been removed for clarity of illustration.

Figure 5:
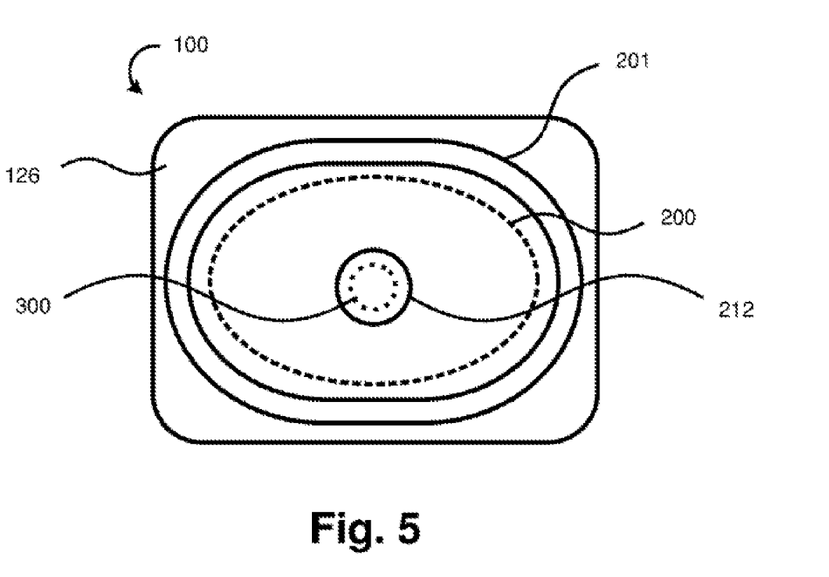
FIG. 5 is a top plan view of the electronic drop device of FIG. 1 showing the internal positioning of a drop container within the electronic drop device, according to one or more embodiments.

The drop container 200 may comprise a nozzle 300. The drop container 200 may be inserted nozzle-first into the electronic drop device 100 such that the nozzle 300 may partially or fully enter the central opening 212 of the curved floor 202. As noted earlier, the drop container 200 may also be inserted rear first such the the nozzle 300 sits central within or proximal to the central opening 212. Reference is now made to FIG. 5, which is a top elevational view of the electronic drop device 100 of FIG. 1 showing the internal positioning of the drop container 200 within the electronic drop device 100, according to one or more embodiments. As shown in FIG. 5, the nozzle 300 of the drop container 200 may be positioned central and proximal to the central opening 212 of the curved floor 202A, B. Though the profile of the drop container 200 is shown to be oval in FIG. 5, the drop container 200 may be of any shape.

The electronic drop device 100 generally operates by first determining a suitable position of the electronic drop device 100 through the accelerometer 114, which activates the electronic drop device 100 once movement is detected. If the electronic drop device 100 is held to the eye and the head is tilted and in the correct position as detected by the accelerometer 114, the electronic control unit 108 activates the color sensor 102 and the color sensor 104, which begin recording color values. The microcontroller 108 may store a number of a predetermined values for orientations, positions, colors, etc. in a database that may be utilized during any determination of any condition of the electronic drop device 100 or drop container 200, such as when the electronic drop device 100 is in a suitable position for drop administration, when an eye 204 is exposed to drop administration, or which kind of substance is contained within the drop container 200. Such determinations are based on comparing recorded values to predetermined values in the database. Since predetermined values are stored in the electronic drop device 100, a wired or wireless connection to another data processing device or remote server may not be necessary. Alternately, to access updates for predetermined values, a network connection to a remote server or other repository may be used.

Figure 6:
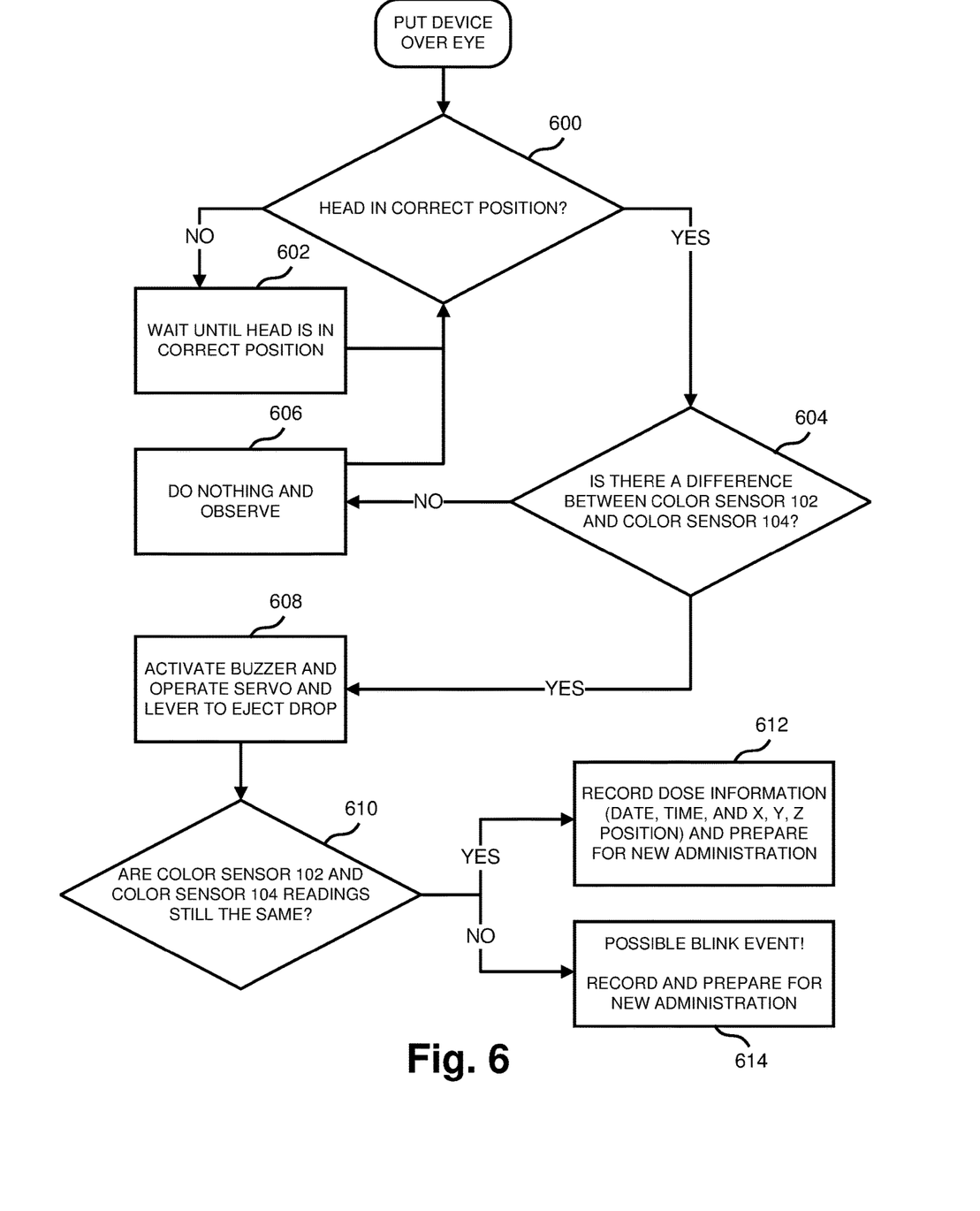
FIG. 6 is a process diagram of a method of administration of the electronic drop device of FIG. 1, according to one or more embodiments.

Reference is now made to FIG. 6 which is a process diagram of a method of administration of the electronic drop device 100 of FIG. 1, according to one or more embodiments. The process diagram of FIG. 6 describes only one embodiment of the electronic drop device 100—other process diagrams comprising a subset of the operations described in FIG. 6 or additional operations or other operations not shown are within the scope of the exemplary embodiments described herein.

In variable 600, the accelerometer 114 is polled and the electronic control unit 108 determines whether the head (i.e. the user's head and subsequently, the electronic drop device 100) is tilted correctly for proper administration of drops 210 from the drop container 200. If not, the process proceeds to state 602, in which the electronic drop device 100 is configured to wait until the head is in the correct position for proper drop administration. If yes, the process proceeds to variable 604, in which the color sensor 102 and the color sensor 104 are polled and the electronic control unit 108 determines whether there is a difference between data retrieved from the color sensor 102 and data retrieved from the color sensor 104. If there is not a difference, the process proceeds to state 606, in which the electronic control unit 108 is configured to do nothing and proceed back to variable 600. If there is a difference, the process proceeds to state 608, in which the piezo buzzer 118 is activated and the servo 110 is activated to either operate the lever arm 112 and compress the external wall of the drop container 200 to eject a drop 210. Alternatively, according to an alternative embodiment, the servo 110 is activated to rotate its gear shaft 220 and attached gear 222 causing rotation and subsequent movement of the servo 110 and its attached rigid floor 218 to compress the external walls of the drop container 200 to eject a drop 210. The process then proceeds to variable 610, in which the electronic control unit 108 is configured to check whether the readings from the color sensor 102 and the color sensor 104 are still the same after administration of the drop 210. If yes, then the process proceeds to state 612, in which dose information (date, time, and XYZ position from the accelerometer 114) is recorded and the electronic drop device 100 prepares for administration of further drops. If not, then the process proceeds to state 614, in which a possible blink event is detected and recorded and the electronic drop device 100 prepares for administration of further drops.

In normal human anatomy, for every human there is a color difference between the sclera (typically white) and iris (typically amber, blue, grey, brown, green, hazel) of the eye 204. When the eye 204 is open, color sensors 102-104 will record different color values in RGB format. However when the eye 204 is closed, the readings reported by each color sensor 102-104 will be the same in all individuals without any eyelid skin discolorations. The RGB values are sent to the electronic control unit 108 which is programmed to interpret said values.

Additionally, there is a marked difference between the right eye socket and the left eye socket, specifically, a downward slope to the sides of the face. When positioning the electronic drop device 100 above the eye 204, the accelerometer 114 may capture different orientation information based on whether the eye 204 is a right eye or a left eye. A comparison of such orientation information or indicia to predetermined or calculated values for the right eye and the left eye may enable an algorithm or logic encoded into the microcontroller 108 to distinguish between administration of drops 210 to the right eye or the left eye.

If there is a substantive difference between the readings from each color sensor 102-104, it is assumed the eye 204 is open and a signal is optionally sent to the piezo buzzer 118, which beeps to alert to the individual that proper position has been achieved and the electronic drop device 100 is ready to administer one or more drops 210 into the eye 204. This is followed by activation of the servo 110, which subsequently mechanically moves according to any number of embodiments as has been described to compress the drop container 200 to squeeze the drops 210 through the nozzle 300 of the drop container 200 and through the central opening 212 of the housing 126. Conversely, if the readings are similar, it is assumed the eye 204 is covered by the eyelid and no ejection occurs.

Substantive difference is best determined by comparing the absolute differences in the RGB values obtained from the color sensors 102-104. If the relative difference of any value is more than a defined threshold, it is deemed to be substantively different. Any number and type of mathematical equations and statistical models may be employed to determine if a substantive difference exists. The actual threshold level that will trigger activation of the servo 110 is based on prior testing and can be adjusted depending on many factors, such as the type of color sensors 102-104 employed, an individual's unique eye appearance, level of accuracy preferred, amongst others.

Figure 7:
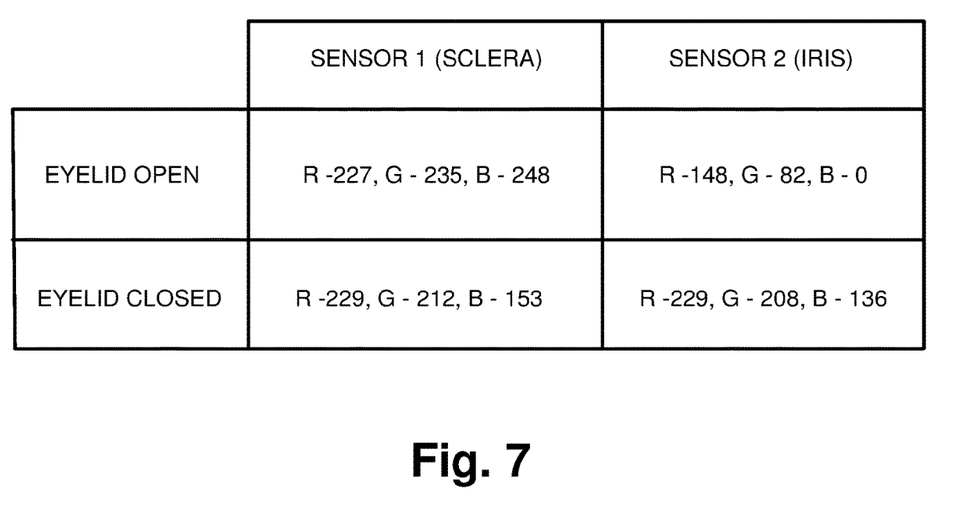
FIG. 7 is a table showing sample measurements collected from the color sensors of the electronic drop device of FIG. 1, according to one or more embodiments.

Reference is now made to FIG. 7 which is a table showing sample measurements collected from the color sensors 102-104 of the electronic drop device 100 of FIG. 1, according to one or embodiments. FIG. 7 shows one example of readings from the color sensors 102-104. When the eyelid of eye 204 is open, the readings are dissimilar and presumed due to an open-eye state. The action of the electronic control unit 108 will be to activate the servo 110 according to any number of embodiments to eject one or more drops 210 from the drop container 200. When the eye 204 is closed, the readings are similar in this exemplary individual with pale brown eyelid skin—thus, no activation of servo 110 occurs.

Figure 8:
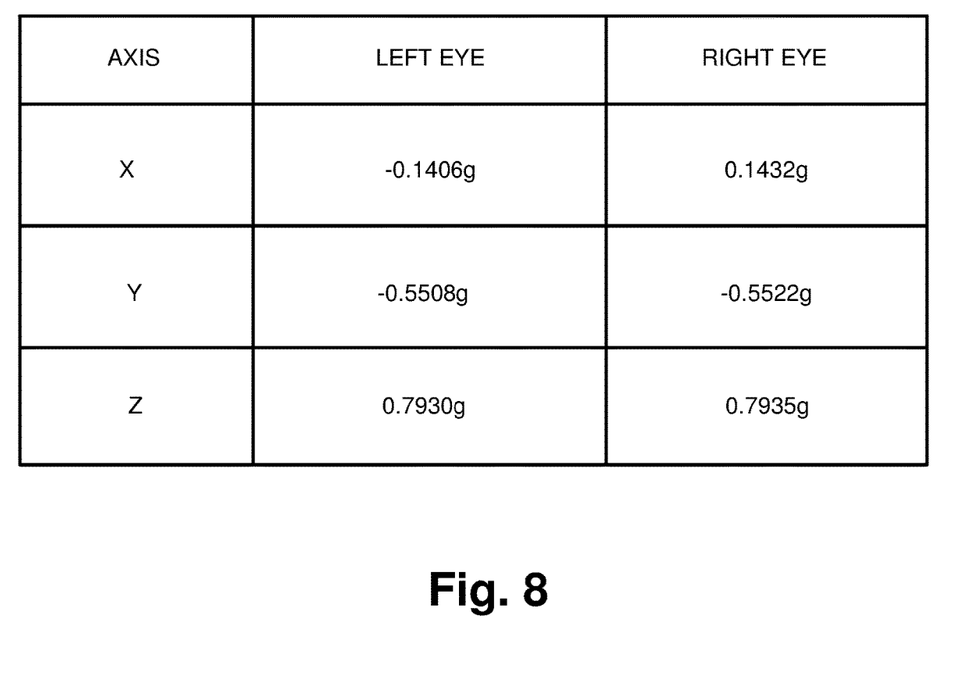
FIG. 8 is a table showing sample readings from the accelerometer of the electronic drop device of FIG. 1, according to one or more embodiments.

Reference is now made to FIG. 8 which is a table showing sample readings from the accelerometer 114 of the electronic drop device 100 of FIG. 1, according to one or more embodiments. The color sensors 102-104 continuously report RGB color values so long as the accelerometer 114 reports that the electronic drop device 100 is held in proper position. The accelerometer 114 communicates X, Y, and Z acceleration values to the electronic control unit 108 and thus may be used to interpret the orientation (X, Y, Z values) of the electronic drop device 100 in three-dimensional space. Such an interpretation may be aided by a gyroscope, magnetometer, or other sensors in an inertial measurement unit (IMU). Based on the X, Y, and Z values, the electronic control unit 108 may also identify which eye 204 is involved in the administration of the drops 210. For most individuals, left eye vs. right eye will produce at least one reverse (negative) value on either of the X, Y, or Z axis due to the anatomical downward tilt of each eye socket producing mirror images of each socket that are titled downward and outward from the midline of the face.

In the event of an ejection, the electronic control unit 108 observes the readings for approximately one to two seconds, the approximate length of time it will take for an ejected eye drop 210 to reach the surface of the eye 204. If the readings of the color sensors 102-104 remain constant, it is assumed the eye 204 remained open and successful eye drop 210 administration is recorded. Conversely, if the readings change following ejection of the drop(s) 210, it is assumed that an eyelid closure (blink event) occurred and the same is recorded as an unsuccessful administration. In this way, the electronic drop device 100 may detect if a drop 210 actually reached the surface of the eye 204 and may prepare for the next dose. From start to finish, the entire operational sequence occurs without any manual input from the user.

To aid tracking and identification of each drop container 200 inserted into the electronic drop device 100, the color sensor 106 in FIG. 2 may be disposed within the housing 126 of the electronic drop device 100 to detect the color of the contents of the drop container 200 or the color of the cap. In the US for example, the caps of prescription multi-dose eye drop bottles are labelled either as tan, pink, gray, red, green, yellow & blue, purple and orange, turquoise to represent anti-microbials, steroids, non-steroidal anti-inflammatories, mydriatics, miotics, beta blockers, adrenergic agonists, and prostaglandin analogues respectively. Patients are typically on only one medication from each category. To detect the color of the cap of the medications, the color sensor 106 detects the color of the eye drop cap upon insertion of the drop container 200 into the electronic drop device 100 or while it is being removed. The color sensor 106 may also determine the color of the body of the drop container 200 (typically clear or cloudy). By detecting the color of the cap or drop container 200 and comparing to preset values for each medication, the device can track and identify any drop container 200 inserted in and potentially flag suspicious or potentially counterfeit medications. Additionally by strategically placing the color sensor 106 near the nozzle 300, it can be configured to detect and alert when the drop container 200 contents are almost empty and needs to be replaced.

While the embodiments described thus far have included three color sensors 102, 104, 106, other implementations are possible. The electronic drop device 100 may be operated with just one or none of the color sensors 102-106 described above. In another embodiment, the blink event may be determined by measuring changes in reflected sound, reflected pressure, recognition of changes in eye structures such as pupillary dilation and constriction or by recording actual images of the eye 204. Any of these alternatives may be combined with an accelerometer 114 to communicate with the servo 110 or other electromechanical combination to compress the external walls of the drop container 200 to dispense the drops 210.

Additionally, while the purpose of the servo 110 in combination with the lever arm 112 or rack 224 A,B and pinion assembly (or electromechanical compressing assembly 110) is to compress the drop container 200, the servo 110 functionality may be substituted in yet another embodiment with a cam and motor assembly or any combination of servos, cams, motors, gears, gearbox assemblies, driveshafts, magnets, electromagnets, sensors, in any type of electromechanical combination to compress the external walls of the drop container 200.

Each time the electronic drop device 100 is turned on, all events are continuously recorded by the electronic control unit 108, which may transmit the data via the Bluetooth® module 116 to any network-enabled mobile device application or other data processing device capable of pairing via Bluetooth®. The data may then be uploaded to a remote or cloud-based server through a network (e.g. a wide-area network, such as the Internet). While Bluetooth® technology has been described thus far due to its current cost-benefit ratio and its simple smart phone pairing interface, the electronic drop device 100 may also utilize a different wireless interface, such as RFID, cellular radio (GSM or CDMA), WiFi, ZigBee, Z-Wave, sub-GHz, or any other proprietary or standardized wireless radio or wired protocol. Once uploaded, the information may be accessible by anyone, anywhere, on any suitable device including but not limited to desktop computers, laptops, smartphones, smart watches, and other hand held smart electronics and wearable hardware. If paired to a smart phone the accompanying app will also provide detailed information such as what medication has been given, when the next dose is due, number of refills to name a few.

Figure 9:
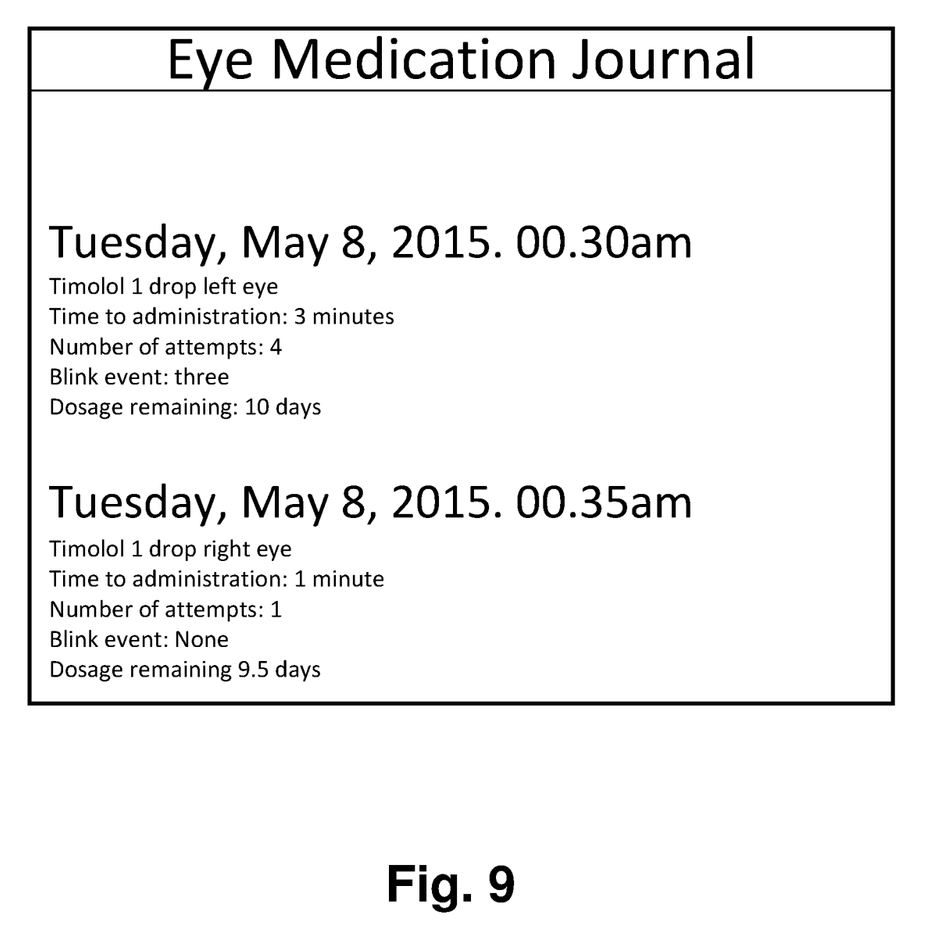
FIG. 9 is an exemplary log generated from the data collected by the sensors of the electronic drop device of FIG. 1, according to one or more embodiments.

At the discretion of the prescribing doctor, the preset dosing instructions may be changed and/or customized to fit the individual needs of the patient. For example, the prescribing doctor or other qualified healthcare worker may change the number of drops 210 dispensed per dose, change the time when medications are due, shorten or extend the expiration date (date after which the device may not be used) to name a few of several options. Reference is now made to FIG. 9 which is an exemplary log generated from the data collected by the sensors of the electronic drop device 100 of FIG. 1, according to one or more embodiments. FIG. 9 is an example of a web interface showing a log viewable by a prescribing doctor.

In addition, utilizing the built-in internet connectivity of the electronic drop device 100, the doctor or any qualified healthcare provider may view in real-time a patient's medication log (see FIG. 9) and make changes remotely based on what information is reported from the electronic drop device 100. For example, if the electronic drop device 100 reports that the patient has missed several doses, the physician or other qualified healthcare provider via a web-based interface may make changes to the dosing schedule to compensate for missing doses. This may occur with or without the patient's involvement, allowing for a precise and more proactive medication management platform.

From the description provided, it should be apparent that the electronic drop device 100 provides an automatic, yet secure and precise means of dispensing any class or type of eye drops including ophthalmic anesthetic eye drops such as proparacaine, cocaine, procaine, tetracaine, hexylcaine, bupivacaine, lidocaine, benoxinate, mepivacaine, prilocaine and etidocaine in any strength or combination. Examples of eye drops include anti-infectives, anti-inflammatories/steroids, nonsteroidal anti-inflammatories, cycloplegics, mydratics, miotics, beta-blockers, adrenergic agonists, carbonic anhydrase inhibitors, prostaglandin analogues, immunosuppressives and all ocular lubricants (artificial tears). Given the current state of art in treating eye diseases and injuries, this electronic drop device 100 opens a new frontier in the treatment of ocular diseases and injuries.

While the electronic drop device 100 embodiments described so have focused on its configuration as an ophthalmic dispensing device, as previously discussed, this is not by any means supposed to be limiting. The same portable electronic drop device 100 can be configured for any application including automatically dispensing hand creams, oral liquid medicines, condiments etc., and would retain most if not all of the same transformative features. When configured for other applications, some features like the curved rim 201 or the curved floor 202 A, B or passageways 206 A, B or color sensors 102, 104, 106 may or may not be necessary.

Furthermore while the object of this invention has been discussed in reference to an individual, this entire electronic drop device 100 and management system and all details contained herein is also applicable to dogs, cats and any other animals requiring administration of any liquid, semiliquid or gaseous substance.

Although the present embodiments have been described with reference to specific example embodiments, it will be evident that various modifications and changes may be made to these embodiments without departing from the broader spirit and scope of the various embodiments. It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The various devices and modules described herein may be enabled and operated using hardware circuitry (e.g., CMOS based logic circuitry), firmware, software or any combination of hardware, firmware, and software (e.g., embodied in a non-transitory machine-readable medium). For example, the various electrical structure and methods may be embodied using transistors, logic gates, and electrical circuits (e.g., application specific integrated (ASIC) circuitry and/or Digital Signal Processor (DSP) circuitry).

What is claimed is:

1. An apparatus for automatically administering drops comprising:
   a microcontroller communicatively coupled to an accelerometer;
   a housing with a contiguous curved rim, suitable for accommodating the microcontroller, the accelerometer, and optionally, a drop-dispenser container with a nozzle configured to be directed at an eye;
   the housing having a central opening through which the nozzle of the drop-dispenser container is inserted;
   the curved rim contiguous with the housing structurally shaped to adapt and follow the bony rim of an eye socket to provide a fixed position for operation; and
   an electromechanical compressing assembly disposed within the housing and communicatively coupled to the microcontroller such that operation of the electromechanical compressing assembly causes the electromechanical compressing assembly to gradually push against an external wall of the drop-dispenser container,
   whereupon detection of a predetermined orientation of the apparatus through the accelerometer, the microcontroller is configured to self-actuate the electromechanical compressing assembly to compress the drop-dispenser container to a calculated degree such that said compression of the drop-dispenser container causes the drop-dispenser container to administer one or more drops of liquid or non-liquid substances contained within the drop-dispenser container.

2. The apparatus of claim 1, further comprising:
   a wireless interface communicatively coupled to the microcontroller and configured to communicate event data generated by the micro controller to a network-enabled data processing device directly or over a network, wherein the event data comprises at least one of: a type of medication contained within the drop-dispenser container, dosage information, occurrence of blink events, remaining dosage, number attempts to administer a dose, time of administration of dosage, and time to administer dosage.

3. The apparatus of claim 1, further comprising:
   a color sensor communicatively coupled to the microcontroller configured to detect a color of a portion of the drop-dispenser container, said color being associated with a type of substance contained within the drop-dispenser container.

4. The apparatus of claim 1, further comprising:
   one or more color sensors communicatively coupled to the microcontroller, the one or more color sensors to detect a color, wherein operation of the microcontroller additionally depends on an approximate match between the color and a predetermined range of colors.

5. The apparatus of claim 4, further comprising:
   one or more passageways of a curved rim for improving consistency in detection of the color, wherein the one or more passageways are optionally fitted with a lens for focusing light to the one or more color sensors.

6. The apparatus of claim 1, further comprising:
   a display screen communicatively coupled to the microcontroller for displaying patient-related information, including physician-recommended dosage, and drop administration reminders.

7. A method of automatically administering drops through an electronic drop-dispensing device, comprising:
   detecting, through a microcontroller communicatively coupled to an accelerometer, a predetermined orientation of the electronic drop-dispensing device;
   guiding a curved rim end portion contiguous with the housing of the electronic drop-dispensing device structurally shaped to adapt and follow the bony rim of an eye socket into a predetermined orientation position over an eye;
   based upon detecting the predetermined orientation, self-actuating, through the microcontroller, an electromechanical compressing assembly communicatively coupled to the microcontroller such that operation of the electromechanical compressing assembly causes the electromechanical compressing assembly to automatically compress a drop-dispenser container such that said compression causes the drop-dispenser container to administer one or more drops of liquid or nonliquid substances contained within the drop-dispenser container through the housing configured to have a central opening through which the nozzle of the drop-dispenser container is inserted.

8. The method of claim 7, further comprising:
   communicating, through a wireless interface communicatively coupled to the microcontroller, an event data to a network-enabled data processing device directly or over a network.

9. The method of claim 7, further comprising:
   generating event data through the micro controller, such event data comprising at least one of: a type of medication contained within the drop-dispenser container, dosage information, occurrence of blink events, remaining dosage, number attempts to administer a dose, time of administration of dosage, and time to administer dosage.

10. The method of claim 7, further comprising:
    wherein operating the electromechanical compressing assembly is additionally based upon detecting an approximate match between a color detected by one or more color sensors communicatively coupled to the microcontroller and a predetermined range of colors.

11. The method of claim 10 further comprising:
    immediately after operating the electromechanical compressing assembly, detecting a blink event based on determining whether the color and another color detected by the one or more color sensors remained mismatched during the operation of the electromechanical compressing assembly.

12. The method of claim 7, further comprising:
    displaying, through a display screen communicatively coupled to the microcontroller, patient-related information, including physician-recommended dosage, and drop administration reminders.

13. A drug-device combination apparatus for automatically administering drops comprising:
    a microcontroller communicatively coupled to an accelerometer;
    a housing with a contiguous curved rim, suitable for accommodating the microcontroller, the accelerometer, and an ophthalmic medication container with a nozzle configured to be directed to an eye;
    the housing having a central opening through which the nozzle of the ophthalmic medication container is inserted;

the curved rim contiguous with the housing structurally shaped to adapt and follow the bony rim of an eye socket to provide a fixed position for operation; and an electromechanical compressing assembly disposed within the housing and communicatively coupled to the microcontroller such that operation of the electromechanical compressing assembly causes the electromechanical compressing assembly to gradually push against the external wall of the ophthalmic medication container, whereupon detection of a predetermined orientation of the apparatus through the accelerometer, the microcontroller is configured to self actuate the electromechanical compressing assembly to compress the ophthalmic medication container to a calculated degree such that said compression of the ophthalmic medication container causes the ophthalmic medication container to administer one or more drops of liquid or non-liquid substances contained within the ophthalmic medication container.

14. The apparatus of claim 13, further comprising:

a wireless interface communicatively coupled to the microcontroller and configured to communicate event data generated by the micro controller to a network-enabled data processing device directly or over a network, wherein the event data comprises at least one of: a type of medication contained within the drop-dispenser container, dosage information, occurrence of blink events, remaining dosage, number attempts to administer a dose, time of administration of dosage, and time to administer dosage.

15. The apparatus of claim 13, further comprising:

one or more color sensors communicatively coupled to the microcontroller, the one or more color sensors to detect a color, wherein operation of the microcontroller additionally depends on an approximate match between the color and a predetermined range of colors.

16. The apparatus of claim 15, further comprising:

one or more passageways of a curved rim for improving consistency in detection of the color, wherein one or more passageways are optionally fitted with a lens for focusing light to the one or more color sensors.

17. The apparatus of claim 13, further comprising:

a display screen communicatively coupled to the microcontroller for displaying patient-related information, including physician-recommended dosage, and drop administration reminders.

\* \* \* \* \*